United States Patent
Limma et al.

(10) Patent No.: US 8,088,042 B2
(45) Date of Patent: Jan. 3, 2012

(54) METHOD, SYSTEM, MEASUREMENT DEVICE AND RECEIVING DEVICE FOR PROVIDING FEEDBACK

(75) Inventors: Ilkka Limma, Kempele (FI); Ville Kampman, Oulu (FI); Hannu Moilanen, Oulu (FI)

(73) Assignee: Elisa Oyj, Helsinki (FI)

( * ) Notice: Subject to any disclaimer, the term of this patent is extended or adjusted under 35 U.S.C. 154(b) by 338 days.

(21) Appl. No.: 10/581,314

(22) PCT Filed: Dec. 7, 2004

(86) PCT No.: PCT/FI2004/000741
§ 371 (c)(1),
(2), (4) Date: Jul. 7, 2006

(87) PCT Pub. No.: WO2005/053524
PCT Pub. Date: Jun. 16, 2005

(65) Prior Publication Data
US 2008/0108481 A1    May 8, 2008

(30) Foreign Application Priority Data
Dec. 5, 2003 (FI) .................................... 20031777

(51) Int. Cl.
*A63B 71/00* (2006.01)
(52) U.S. Cl. .................... 482/8; 482/1; 482/9; 482/901; 434/247
(58) Field of Classification Search .................. 482/1–9, 482/900–902; 434/247
See application file for complete search history.

(56) References Cited

U.S. PATENT DOCUMENTS

| | | | | |
|---|---|---|---|---|
| 4,708,337 A | * | 11/1987 | Shyu | 482/54 |
| 4,828,257 A | * | 5/1989 | Dyer et al. | 482/5 |
| 4,919,418 A | * | 4/1990 | Miller | 482/6 |
| 4,934,694 A | * | 6/1990 | McIntosh | 482/9 |
| 5,451,192 A | * | 9/1995 | Hefele | 482/52 |
| 5,690,582 A | * | 11/1997 | Ulrich et al. | 482/4 |
| 5,807,267 A | * | 9/1998 | Bryars et al. | 600/500 |
| 5,839,901 A | * | 11/1998 | Karkanen | 434/127 |
| 5,890,128 A | * | 3/1999 | Diaz et al. | 705/2 |
| 5,890,995 A | * | 4/1999 | Bobick et al. | 482/4 |
| 5,941,837 A | * | 8/1999 | Amano et al. | 600/595 |
| 5,989,188 A | * | 11/1999 | Birkhoelzer et al. | 600/300 |
| 6,013,007 A | * | 1/2000 | Root et al. | 482/8 |
| 6,018,677 A | * | 1/2000 | Vidrine et al. | 600/520 |
| 6,032,108 A | * | 2/2000 | Seiple et al. | 702/97 |
| 6,287,262 B1 | * | 9/2001 | Amano et al. | 600/500 |
| 6,513,532 B2 | * | 2/2003 | Mault et al. | 600/595 |
| 6,515,593 B1 | * | 2/2003 | Stark et al. | 340/870.07 |

(Continued)

FOREIGN PATENT DOCUMENTS

WO    01/42809 A2    6/2001

*Primary Examiner* — Glenn Richman
(74) *Attorney, Agent, or Firm* — The Nath Law Group; Jerald L. Meyer; Stanley P. Protigal

(57) ABSTRACT

A method, system, measurement device and receiving device for providing feedback relating to an activity to at least one individual. In the method, activity information relating to an activity is measured with a measurement device. Activity information is transmitted to a receiving device via a communication link. The receiving device selects from the received activity information a predefined set of pieces of activity information and provides the at least one individual with feedback based on the selected activity information.

29 Claims, 3 Drawing Sheets

U.S. PATENT DOCUMENTS

| | | | |
|---|---|---|---|
| 6,592,502 B1 * | 7/2003 | Phillips | 482/143 |
| 6,605,044 B2 * | 8/2003 | Birnbaum | 600/500 |
| 6,671,736 B2 * | 12/2003 | Virine et al. | 709/238 |
| 6,675,041 B2 * | 1/2004 | Dickinson | 600/509 |
| 6,697,048 B2 * | 2/2004 | Rosenberg et al. | 345/161 |
| 6,736,759 B1 * | 5/2004 | Stubbs et al. | 482/8 |
| 6,749,537 B1 * | 6/2004 | Hickman | 482/8 |
| 6,783,482 B2 * | 8/2004 | Oglesby et al. | 482/54 |
| 6,790,178 B1 * | 9/2004 | Mault et al. | 600/300 |
| 6,798,378 B1 * | 9/2004 | Walters | 342/357.06 |
| 6,906,533 B1 * | 6/2005 | Yoshida | 324/692 |
| 6,921,351 B1 * | 7/2005 | Hickman et al. | 482/8 |
| 6,950,695 B2 * | 9/2005 | Chen | 600/509 |
| 6,982,700 B2 * | 1/2006 | Rosenberg et al. | 345/157 |
| 7,056,265 B1 * | 6/2006 | Shea | 482/8 |
| 7,072,789 B2 * | 7/2006 | Vock et al. | 702/141 |
| 7,166,062 B1 * | 1/2007 | Watterson et al. | 482/8 |
| 7,187,960 B2 * | 3/2007 | Abreu | 600/310 |
| 7,220,220 B2 * | 5/2007 | Stubbs et al. | 482/72 |
| 7,229,416 B2 * | 6/2007 | Chen | 600/500 |
| 7,232,416 B2 * | 6/2007 | Czernicki | 600/595 |
| RE39,906 E * | 11/2007 | Roston et al. | 318/561 |
| 7,305,303 B2 * | 12/2007 | Soehren et al. | 701/221 |
| 7,312,766 B1 * | 12/2007 | Edwards | 345/8 |
| 7,344,508 B2 * | 3/2008 | Surina | 600/587 |
| 7,359,624 B2 * | 4/2008 | Adams et al. | 386/124 |
| 7,373,820 B1 * | 5/2008 | James | 73/488 |
| 2003/0022140 A1 * | 1/2003 | Chang | 434/247 |
| 2003/0065257 A1 * | 4/2003 | Mault et al. | 600/407 |
| 2004/0046692 A1 | 3/2004 | Robson et al. | |
| 2004/0102684 A1 * | 5/2004 | Kawanishi et al. | 600/300 |
| 2004/0198554 A1 * | 10/2004 | Orr et al. | 482/8 |
| 2004/0220017 A1 * | 11/2004 | Gordon et al. | 482/8 |
| 2004/0224822 A1 * | 11/2004 | Verheem | 482/8 |
| 2005/0032608 A1 * | 2/2005 | Glusco | 482/9 |
| 2005/0107218 A1 * | 5/2005 | Chuang et al. | 482/45 |
| 2005/0124463 A1 * | 6/2005 | Yeo et al. | 482/8 |
| 2005/0130802 A1 * | 6/2005 | Kinnunen et al. | 482/8 |
| 2005/0164857 A1 * | 7/2005 | Black | 482/148 |
| 2005/0197237 A1 * | 9/2005 | Chen | 482/8 |
| 2005/0209050 A1 * | 9/2005 | Bartels | 482/8 |
| 2005/0209051 A1 * | 9/2005 | Santomassimo et al. | 482/8 |
| 2005/0233859 A1 * | 10/2005 | Takai et al. | 482/3 |
| 2005/0233861 A1 * | 10/2005 | Hickman et al. | 482/8 |
| 2005/0272564 A1 * | 12/2005 | Pyles et al. | 482/54 |
| 2006/0020177 A1 * | 1/2006 | Seo et al. | 600/300 |
| 2006/0052727 A1 * | 3/2006 | Palestrant | 600/595 |
| 2006/0063644 A1 * | 3/2006 | Yang | 482/4 |
| 2006/0098772 A1 * | 5/2006 | Reho et al. | 377/24.2 |
| 2006/0183602 A1 * | 8/2006 | Astilean | 482/7 |
| 2006/0183603 A1 * | 8/2006 | Astilean | 482/8 |
| 2006/0189437 A1 * | 8/2006 | Cohen et al. | 482/7 |
| 2006/0229163 A1 * | 10/2006 | Waters | 482/8 |
| 2007/0021269 A1 * | 1/2007 | Shum | 482/8 |
| 2007/0033068 A1 * | 2/2007 | Rao et al. | 705/2 |
| 2007/0033069 A1 * | 2/2007 | Rao et al. | 705/2 |
| 2007/0142177 A1 * | 6/2007 | Simms et al. | 482/8 |
| 2007/0173377 A1 * | 7/2007 | Jamsen et al. | 482/8 |
| 2008/0153671 A1 * | 6/2008 | Ogg et al. | 482/3 |
| 2010/0190609 A1 * | 7/2010 | Shum et al. | 482/8 |

* cited by examiner

METHOD, SYSTEM, MEASUREMENT DEVICE AND RECEIVING DEVICE FOR PROVIDING FEEDBACK

FIELD OF THE INVENTION

The present invention relates to providing feedback relating to an activity. In particular, the present invention relates to a novel and improved method, system, measurement device and receiving device for providing feedback relating to an activity to at least one individual.

BACKGROUND OF THE INVENTION

People have always been interested in how they perform in various tasks, e.g. in various sport events. Different manufacturers have provided various kinds of devices that can be used to analyze e.g. a sport event. These devices include e.g. a heart rate monitor, a wrist computer etc.

The Global Positioning System (GPS) provides a service in which by using a special GPS receiver position information can be acquired. The GPS uses a plurality of satellites to determine the position.

There exists a plurality of known solutions that use the GPS to record a path of an activity, e.g. a sport event. Such a data recorder can be afterwards connected to a computer and the performed path, e.g. a run path, can be displayed on a screen of the computer by connecting the recorded position points (coordinates). Furthermore, there exists known solutions that are able to record other quantities into memory of a measurement device. The quantites include e.g. a heart rate during an exercise, temperature etc.

One known solution uses a combination of a wristwatch and a heart rate belt display and/or record the heart rate data. The watch can be connected to a computer after the exercise, and based on the recorded heart rate data, a heart rate curve can be displayed to the user as a function of time. Furthermore, in other solutions it is possible e.g. to determine speed during a recorded path and the length of the recorded path based on the based on the position coordinates provided by the GPS receiver.

In some solutions, a current speed value and a distance travelled so far can be displayed using e.g. a wristwatch.

The problem with the current solutions is that every activity or sport needs a dedicated measurement device that can used to analyse performance.

SUMMARY OF THE INVENTION

According to one aspect of the invention there is provided a method of transmitting measured activity information and providing at least one individual with feedback based on the measured activity information. The method comprises the steps of measuring activity information relating to an activity of with a measurement device; transmitting activity information to a receiving device via a communication link; selecting from the received activity information a predefined set of pieces of activity information with the receiving device; and providing the at least one individual with feedback based on the selected activity information.

In one embodiment of the invention, the step of providing comprising providing the at least one individual at least one activity indicator based on the selected activity information with at least one feed-back device.

In one embodiment of the invention, prior to the step of providing the method further comprising the steps of calculating at least one additional activity indicator based on the at least one selected activity information; and providing the at least one individual individual with the calculated at least one additional activity indicator with the at least one feedback device.

In one embodiment of the invention, the step of providing comprising presenting the at least one activity indicator to the at least one individual as at least one of a graphical form and voice signals.

In one embodiment of the invention, prior to the step of transmitting the method further comprising the step of calculating at least one additional piece of activity information based on the measured activity information.

In one embodiment of the invention, the step of transmitting comprising transmitting activity information according to a communication protocol.

In one embodiment of the invention, the step of providing comprising providing the at least one individual with feedback with the receiving device.

In one embodiment of the invention, the step of providing comprising providing the at least one individual with feedback with at least one device connected to the receiving device.

In one embodiment of the invention, the step of measuring comprising measuring at least one of the following quantities: time, location, altitude, temperature, and heart rate.

According to another aspect of the invention there is provided a measurement device configured to measure and transmit activity information. The measurement device comprises a processor; a plurality of measuring elements configured to measure a plurality of quantities relating to an activity; a memory configured to store measurement data provided by the measuring elements; and a transmitter configured to transmit activity information to at least one receiving device via a communication link according to a communication protocol.

In one embodiment of the invention, the plurality of measuring elements comprises at least one of the following: a GPS receiver, a barometer, a thermometer, and at least one pulse coil configured to measure heart rate.

In one embodiment of the invention, the processor is configured to calculate at least one additional piece of activity information based on the measured activity information; and the transmitter is configured to transmit the calculated activity information via a communication link.

According to another aspect of the invention there is provided a receiving device configured to receive activity information from a measurement device. The receiving device comprises a receiver configured to receive a transmission from the measurement device, wherein the transmission includes activity information measured with the measurement device; a memory configured to store at least one definition based on which a predefined set of pieces of activity information is selected from the received activity information; and a processor configured to select the predefined set of pieces of activity information from the received activity information based on the at least one definition stored on the memory.

In one embodiment of the invention, the receiving device further comprises at least one feedback device configured to provide at least one individual with feedback based on the selected activity information.

In one embodiment of the invention, the receiving device further comprises an output to which at least one feedback device can be connected.

In one embodiment of the invention, the at least one feedback device is configured to provide the at least one individual with at least one activity indicator based on the selected activity information.

In one embodiment of the invention, the processor is configured to calculate at least one additional piece of activity information based on the at least one selected activity information, and the at least one feedback device is configured to provide the at least one individual with the calculated at least one activity indicator.

In one embodiment of the invention, the at least one feedback device is configured to present the at least one activity indicator to the at least one individual as at least one of a graphical form and voice signals.

In one embodiment of the invention, the at least one feedback device comprises at least one of a display, a speaker and an earpiece.

According to another aspect of the invention there is provided a system of transmitting measured activity information and providing at least one individual with feedback based on the measured activity information. The system comprises a measurement device comprising a first processor, a plurality of measuring elements configured to measure a plurality of quantities relating to an activity, a first memory configured to store measurement data provided by the measuring elements, and a transmitter configured to transmit activity information to at least one receiving device via a communication link according to a communication protocol; and a receiving device comprising a receiver configured to receive a transmission from the measurement device, wherein the transmission includes activity information measured with the measurement device, a second memory configured to store at least one definition based on which a predefined set of pieces of activity information is selected from the received activity information, and a second processor configured to select the predefined set of pieces of activity information from the received activity information based on the at least one definition stored on the second memory; and at least one feedback device configured to provide the at least one individual with feedback based on the selected activity information.

In one embodiment of the invention, the plurality of measuring elements comprises at least one of the following: a GPS receiver, a barometer, a thermometer, and at least one pulse coil configured to measure heart rate.

In one embodiment of the invention, the first processor is configured to calculate at least one additional piece of activity information based on the measured activity information; and the transmitter is configured to transmit the calculated activity information via a communication link to the receiving device.

In one embodiment of the invention, the receiving device further comprises at least one feedback device configured to provide at least one individual with feedback based on the selected activity information.

In one embodiment of the invention, the receiving device further comprises an output to which at least one feedback device can be connected.

In one embodiment of the invention, the at least one feedback device is configured to provide the at least one individual with at least one activity indicator based on the selected activity information.

In one embodiment of the invention, the second processor is configured to calculate at least one additional piece of activity information based on the at least one selected activity information, and the at least one feedback device is configured to provide the at least one individual with the calculated at least one activity indicator.

In one embodiment of the invention, the at least one feedback device is configured to present the at least one activity indicator to the at least one individual as at least one of a graphical form and voice signals.

In one embodiment of the invention, the at least one feedback device comprises at least one of a display, a speaker and an earpiece.

The present invention has several advantages over the prior-art solutions. A benefit of the invention is that a single measurement device can be used to transmit all relevant information relating to an activity. The receiving device may then decide what pieces of activity information to use. Due to the aforementioned fact, device manufactures are able to manufacture a variety of different receiving devices depending on the need and use of the device. All devices, however, receive the same transmission from the measurement device and are configured to give feedback to an individual or individuals (e.g. using a display of a device). For example, a cheap receiving device may display just basic feedback values to an athlete, whereas a more expensive receiving device may provide the athlete with a variety of pieces of performance information.

In other words, the invention provides a standard communication interface into which manufacturers of suitable equipment, e.g. wrist watches, mobile terminals, fixed sport stadium displays shall connect to.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Reference will now be made in detail to the embodiments of the present invention, examples of which are illustrated in the accompanying drawings.

Figure 1:
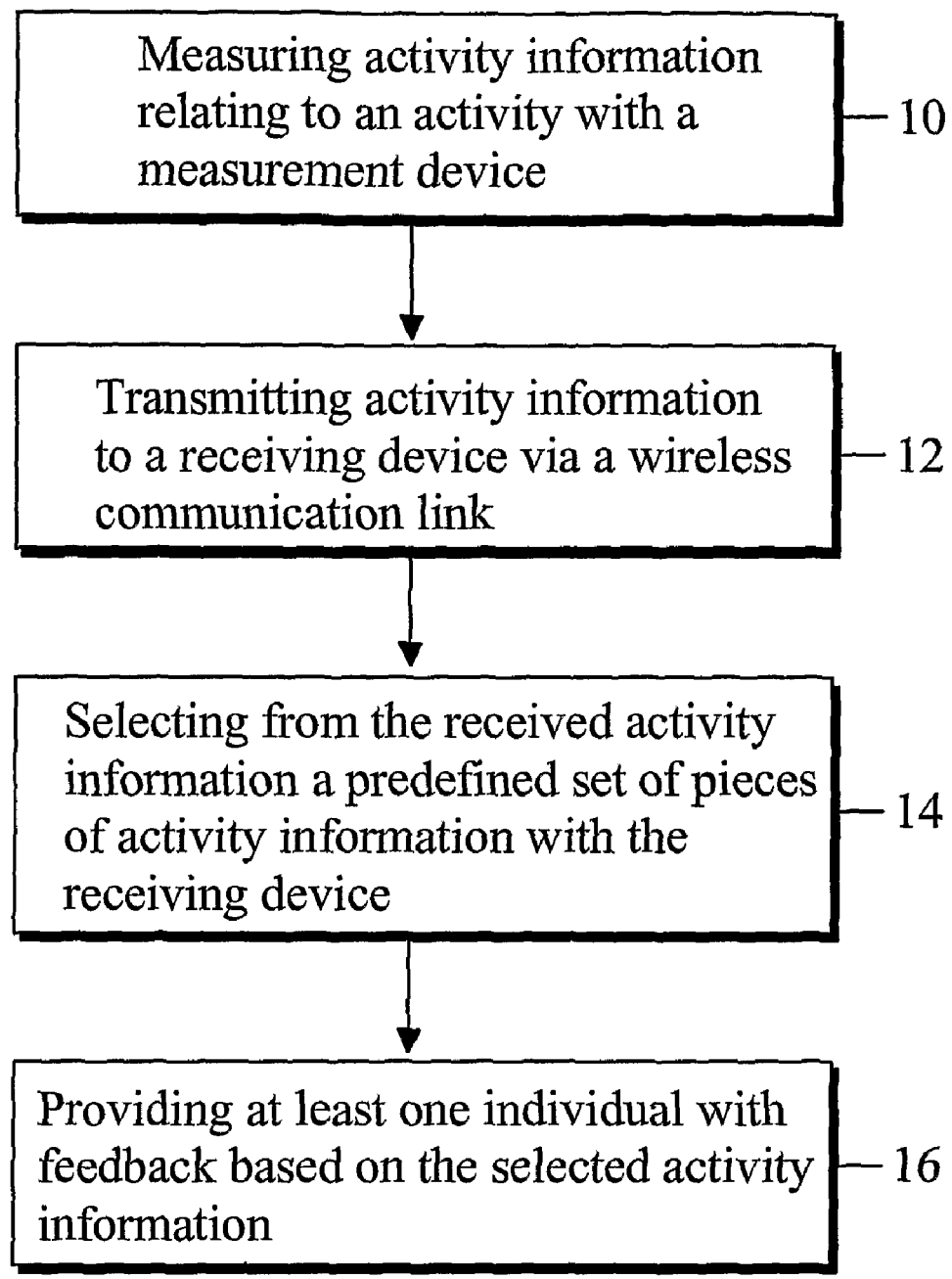
FIG. 1 is a block diagram illustrating one embodiment of a method according to the invention.

FIG. 1 is block diagram illustrating one embodiment of a method according to the invention. As indicated at step 10, activity information relating to an activity is measured with a measurement device. An activity may take any appropriate form, e.g. a run, a ski tour, sailing, cycling etc. A common feature to all these activities is that the user carries a measurement device. The measurement device may be attached to the user or it may alternatively be a stand-alone model. The measurement device measures and records a plurality of quantities, e.g. time, location, altitude, temperature and/or heart rate.

Activity information is then transmitted to a receiving device via a communication link, e.g. a wireless communication link, as indicated at step 12. The receiving device is e.g. a wristwatch, a display panel etc. The wireless communication link refers e.g. to a short-range wireless radio transmission. The receiving device is configured to select a predefined set of pieces of activity information from the transmission, as indicated at step 14. Based on the selected activity information, at least one individual is provided with feedback, as indicated at step 16. The at least one individual may be the aforementioned user himself/herself. In another embodiment, the receiving device may be connected to a separate feedback device or devices, e.g. to a scoreboard providing a plurality of individuals with feedback at the same time.

Figure 2:
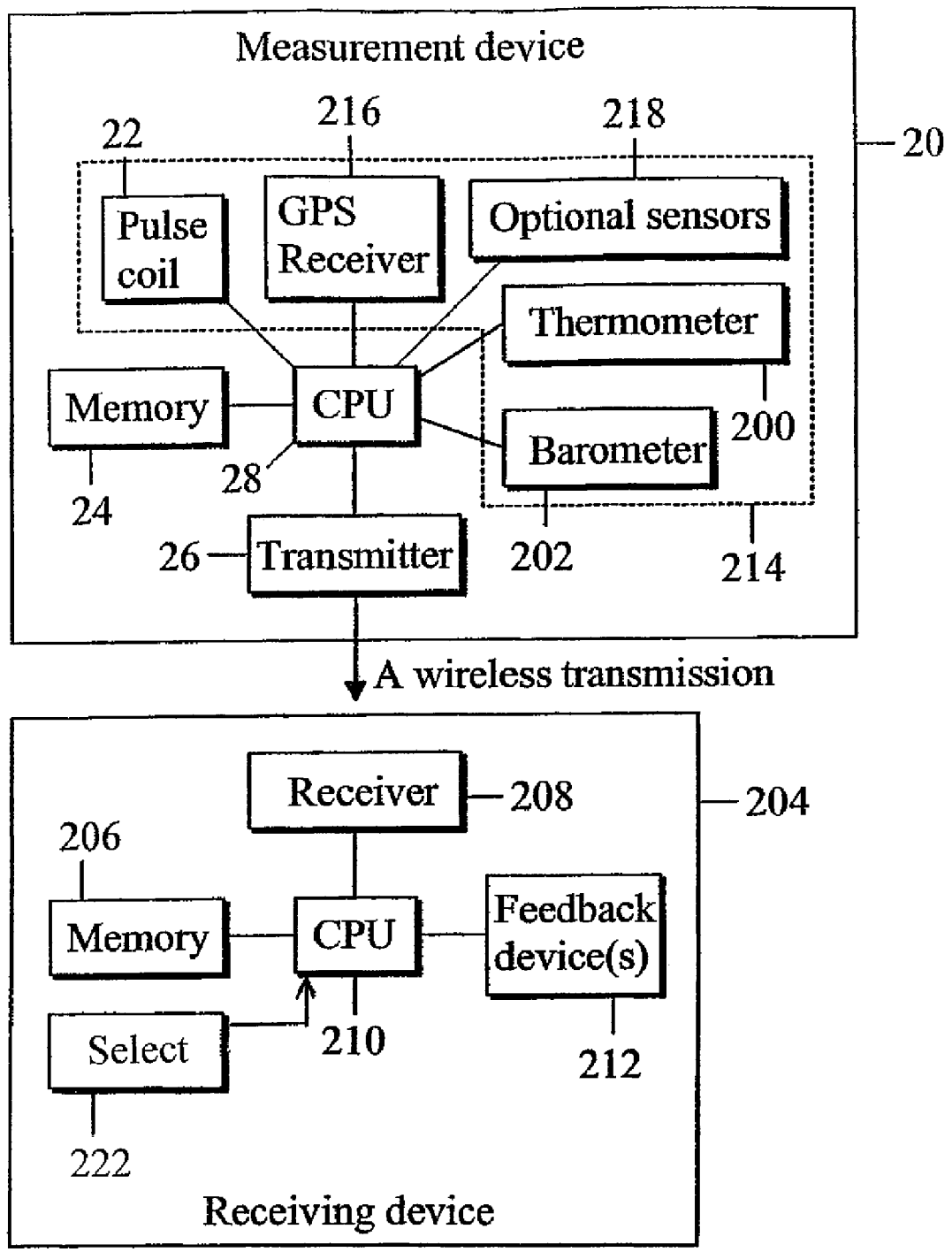
FIG. 2 is a block diagram illustrating one embodiment of a system according to the invention.

FIG. 2 is a block diagram illustrating one embodiment of a system according to the invention. The system of FIG. 2 comprises a measurement device 20 and a receiving device 204. FIG. 2 discloses only relevant elements and components of the measurement device 20 and receiving device in order to illustrate the invention. Therefore, it is evident that the devices may comprise also other elements and components not illustrated in FIG. 2.

Measurement device 20 is in one embodiment a device that can be attached e.g. to an arm of a user, e.g. an athlete. In other embodiments, it may be a stand-alone model that can be mounted to a desired place.

Measurement device 20 comprises a plurality of measuring elements 214. In this embodiment measuring elements 214 include a GPS receiver 216 configured to receive positioning information from a plurality of satellites, a pulse coil or pulse coils 22 configured to measure heart rate based on signals received e.g. from a pulse belt, a thermometer 200 configured to measure temperature and an barometer 202 configured to measure altitude. An element optional sensors 218 refers to any other optional sensor or sensors not disclosed above that can be incorporated into measurement device 20. Each measurement element is connected to a central processing unit 28. The measurement device 20 includes also a memory 24 connected to central processing unit 28. Memory 24 is configured to store measurements from the plurality of measuring elements 214. Furthermore, measurement device 20 includes a transmitter 26. Central processing unit 28 is configured to send with transmitter 26 a set of measured pieces of activity information from memory 24. Activity information refers mainly to measurement information provided by the plurality of measuring elements 214. Activity information may, however, comprise also information that has been calculated using central processing unit 28 based on the measurement results provided by the plurality of measuring elements 214. Such calculated values may include e.g. speed (calculated based on altitude and position information), pitch angle (calculated based on altitude and position information) etc.

The aforementioned activity information is arranged to a predefined form using a communication protocol. A frame of such a communication protocol typically comprises a header, at least one piece of activity information (measurement or calculated value), and a checksum. The communication protocol may also be an adaptive protocol. Any appropriate protocol may be used in the transmission. Transmitter 26 is configured to transmit data to a receiving device 204 via a wireless communication link. The wireless communication link refers e.g. to a short-range wireless radio transmission.

Receiving device 204 receives the transmission from transmitter 26 with a receiver 208. Receiving device 204 further includes a central processing unit 210, a memory 206 and a feedback device 212. Central processing unit 210 has a connection to each of receiver 208, memory 206 and feedback device 212. Memory 206 is configured to store at least one definition based on which a predefined set of pieces of activity information is selected from the received activity information from measurement device 20. Central processing unit 210 is configured to select (at 222) the predefined set of pieces of activity information from the received activity information based on the at least one definition stored on memory 206. Central processing unit 210 may in one embodiment also calculate at least one additional piece of activity information based on the at least one selected activity information. Such calculated values may include e.g. speed (calculated based on altitude and position information), pitch angle (calculated based on altitude and position information) etc.

Feedback device 212 is configured to provide the user of receiving device 204 with feedback based on the selected activity information. Feedback itself refers e.g. to a variety of activity indicators (speed, heart rate, altitude, air pressure temperature, position etc,). In one embodiment feedback is provided visually, i.e. feedback device 212 refers to a display. In another embodiment, feedback refers to sound signals, i.e. feedback device 212 refers e.g. to a speaker or an earpiece.

In FIG. 2 it is illustrated that feedback device 212 is a functional part of receiving device 204. In another embodiment of the invention, receiving device is configured to include an output to which at least one external feedback device may be connected. The output refers e.g. to a wireless or wired output interface towards an external feedback device or devices.

Receiving device 204 refers e.g. to a wristwatch, a display panel or any other type of feedback device that communicates with measurement device 20.

Although FIG. 2 discloses a specific set of measurement elements 214, it is evident that any one of the measuring elements 214 may be replaced with another appropriate element or, alternatively, any one of them may not have to be included in measurement device 20 at all.

Figure 3:
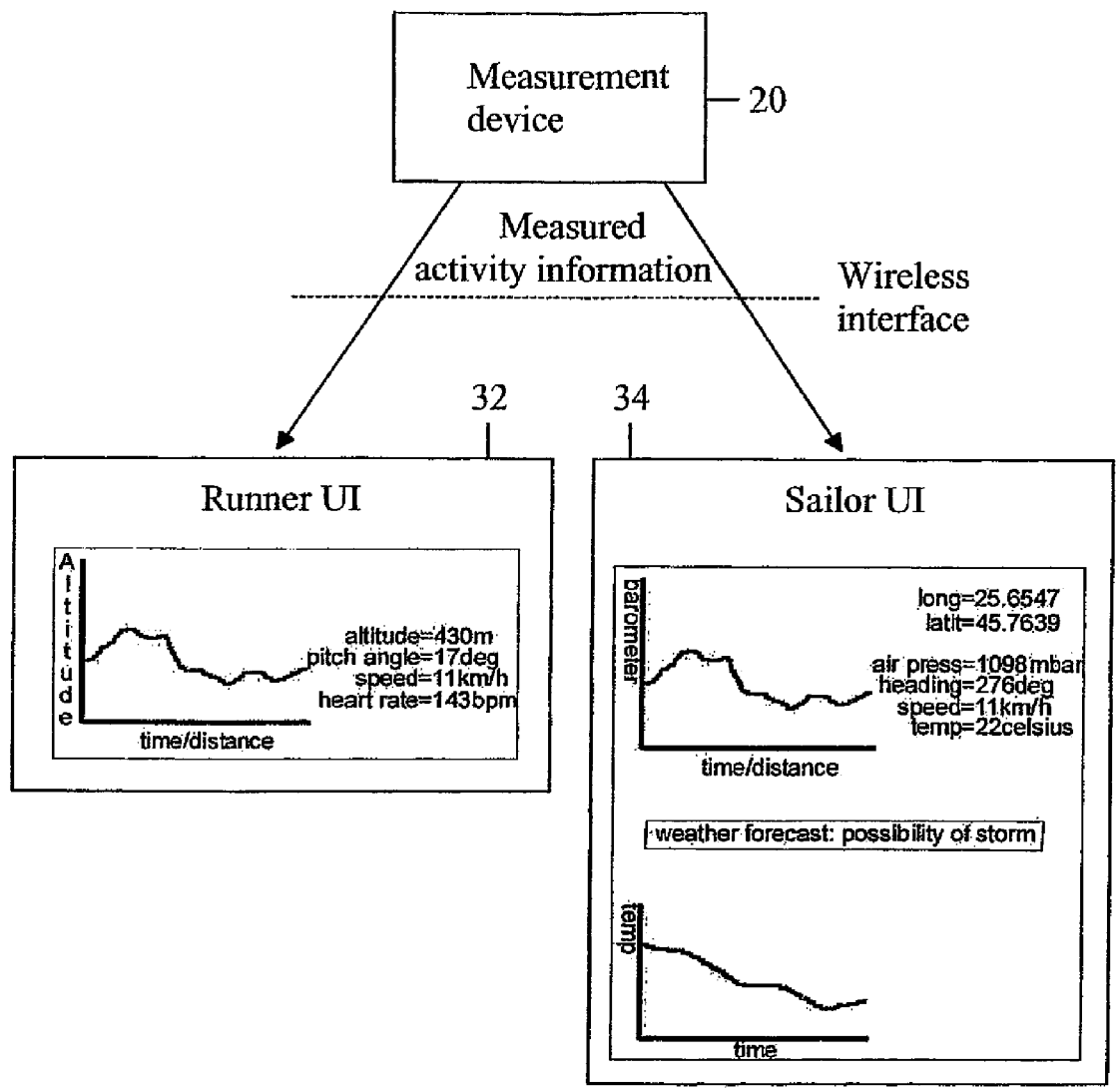
FIG. 3 illustrates one embodiment of possible user interfaces in receiving devices according to the invention.

FIG. 3 illustrates one embodiment of possible user interfaces in receiving devices according to the invention. Furthermore, FIG. 3 discloses a simplified embodiment that yet further illustrates the inventive idea of the invention.

FIG. 3 includes a measurement device 20 that was already discussed in more detail with FIG. 2. FIG. 3 further includes two different user interfaces, a runner user interface 32 and a sailor user interface 34. Runner user interface 32 is typically used in smaller devices, e.g. wristwatches etc. Sailor user interface 34 may be displayed on a larger display. Therefore, it can be used to convey more information to a user. The transmission of measured activity information via a wireless interface was also discussed in more detail with FIG. 2.

Runner user interface 32 shows basic values relating to an activity to the user. These basic values include e.g. altitude, pitch angle, speed and heart rate. Sailor user interface 34 displays more complex values to the user, e.g. longitude and latitude, air pressure, heading, speed, temperature, various graphs etc. It can be seen from FIG. 3 that, for example, information provided by a barometer can be used in different ways for different purposes or sports. A runner wants to see changes in air pressure by means of altitude changes, where as a sailor is also interested in the air pressure itself. Furthermore, air pressure in function of time can be used to forecast a possibility of a storm.

As a summary, FIG. 3 clarifies the fundamental inventive idea of the invention, which provides a standard wireless communication interface into which manufacturers of suitable equipment, e.g. wrist watches, mobile terminals, fixed sport stadium displays shall connect to. Furthermore the size, durability and usability of the user interface device (receiving device) can be designed according to the characteristic of the activity or sport in question.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A method for transmitting measured sports activity information and providing at least one individual with feedback based on the measured sports activity information, wherein the method comprises:

measuring sports activity information with a measurement device comprising a plurality of measuring elements connected to a processing unit;

transmitting, with the measurement device, the measured sports activity information to a receiving device via a short-range wireless radio communication link during the activity, wherein the receiving device provides different user interfaces in different sports or activities, according to the use or purpose of the information for the different sports or activities;

selecting, based on the sport in question, from the received sports activity information a predefined set of pieces of sports activity information with the receiving device based on at least one definition, stored in a memory, of a predefined set of pieces of activity information selected from the measured sports activity information; and providing, through a standard communication interface connection, with the receiving device on a user interface display selected based on the sport in question, the at least one individual with feedback based on the selected sports activity information, wherein, in the case of at least one activity, the user interface display comprises activity-specific information according to the sport in question and comprising geophysical data selected from at least one of a group consisting of longitude and latitude, air pressure, heading, speed, temperature and graphical information, whereby the standard communication interface provides a capability to provide said display size, durability and usability according to the characteristic of said one activity.

2. The method according to claim 1, wherein said providing step comprises providing the at least one individual at least one sports activity indicator based on the selected sports activity information with at least one feedback device.

3. The method according to claim 2, wherein prior to said providing step the method further comprises:
calculating at least one additional sports activity indicator based on the at least one selected sports activity information; and
providing the at least one individual with the calculated at least one additional sports activity indicator with the at least one feedback device.

4. The method according to claim 2, wherein said providing step comprises presenting the at least one sports activity indicator to the at least one individual as at least one of a graphical form and voice signals.

5. The method according to claim 1, wherein prior to said transmitting step the method further comprises:
calculating at least one additional piece of sports activity information based on the measured sports activity information.

6. The method according to claim 1, wherein said transmitting step comprises transmitting sports activity information according to a communication protocol.

7. The method according to claim 1, wherein said providing step comprises providing the at least one individual with feedback with the receiving device.

8. The method according to claim 1, wherein said providing step comprises providing the at least one individual with feedback with at least one device connected to the receiving device.

9. The method according to claim 1, wherein said measuring step comprises measuring at least one of the following quantities:
time;
location;
altitude;
temperature; and
heart rate.

10. The method according to claim 1, wherein the receiving device is carried by the at least one individual.

11. The method according to claim 1, wherein the receiving device comprises stored in its memory at least one definition based on which the predefined set of pieces is selected from the received sports activity information.

12. The method according to claim 1, wherein the sports activity information provided by the measurement device, such as information provided by a barometer, is used in different ways for different sports.

13. The method of claim 1, further comprising providing a standard wireless communication interface for the receiving device to connect to.

14. A measurement device configured to measure and transmit sports activity information, wherein the measurement device comprises:
a processor;
a plurality of measuring elements configured to measure a plurality of quantities relating to a sports activity according to the use or purpose of the information for the sports activity, wherein the plurality of measuring elements comprise at least one of the following:
a GPS receiver;
a barometer;
a thermometer; and
at least one pulse coil configured to measure heart rate;
a memory configured to store measurement data provided by the measuring elements;
a transmitter configured to transmit sports activity information via a short-range wireless radio communication link during the sports activity according to a communication protocol, said transmission of sports activity information subject to a selection by a receiving device based on the sport in question, to at least one receiving device based on at least one definition, stored in the memory, of a predefined set of pieces of activity information selected from the measured sports activity information, wherein, in the case of at least one activity, transmission of sports activity specific to the sport in question comprises activity-specific information comprising geophysical data selected from at least one of a group consisting of longitude and latitude, air pressure, heading, speed, temperature and graphical information; and
a user interface display interface including a standard communication interface connection, permitting connection to a user interface display selected based on the sport in question, thereby providing a capability to provide said display size, durability and usability according to the characteristic of said one activity.

15. The measurement device according to claim 14, wherein the processor is configured to calculate at least one additional piece of sports activity information based on the measured sports activity information; and the transmitter is configured to transmit the calculated sports activity information via a communication link.

16. A receiving device configured to receive sports activity information from a measurement device, wherein the receiving device comprises:
a receiver configured to receive, during a sports activity, a transmission from the measurement device via a short-range wireless radio communication link, wherein the transmission includes sports activity information measured with the measurement device, and the receiver provides different user interfaces in different sports or activities, according to the use or purpose of the information for the different sports or activities, wherein, in the case of at least one activity, the transmission includes sports activity information comprises activity-specific information comprising geophysical data selected from at least one of a group consisting of longitude and latitude, air pressure, heading, speed, temperature and graphical information;

a memory configured to store at least one definition, based on which a predefined set of pieces of sports activity information is selected from the received sports activity information according to the use or purpose of the information for the sports activity;

a processor configured to select the predefined set of pieces of sports activity information from the received sports activity information based on the at least one definition, which is defined based on the sport in question, stored on the memory and connected through a standard communication interface connection; and at least one feedback device connected to the standard communication interface connection and configured to provide at least one individual with feedback on a user interface display based on the selected sports activity information, whereby the standard communication interface provides a capability to provide said display size, durability and usability according to the characteristic of said one activity.

17. The receiving device according to claim 16, wherein the receiving device further comprises an output to which at least one feedback device can be connected.

18. The receiving device according to claim 16, wherein the at least one feedback device is configured to provide at least one individual with at least one sports activity indicator based on the selected sports activity information.

19. The receiving device according to claim 16, wherein the processor is configured to calculate at least one additional piece of sports activity information based on the at least one selected sports activity information, and the at least one feedback device is configured to provide the at least one individual with the calculated at least one sports activity indicator.

20. The receiving device according to claim 16, wherein the at least one feedback device is configured to present the at least one sports activity indicator to the at least one individual as at least one of a graphical form and voice signals.

21. The receiving device according to claim 16, wherein the at least one feedback device comprises at least one of a display, a speaker and an earpiece.

22. A system of transmitting measured sports activity information and providing at least one individual with feedback based on the measured sports activity information, wherein the system comprises:

a measurement device comprising a first processor, a plurality of measuring elements configured to measure a plurality of quantities relating to a sports activity, a first memory configured to store measurement data provided by the measuring elements, and a transmitter configured to transmit sports activity information during the sports activity, according to the use or purpose of the information for the different sports activity, to at least one receiving device based on at least one definition, stored in a memory, of a predefined set of pieces of activity information selected from the measured sports activity information, via a local communication link according to a communication protocol, wherein the plurality of measuring elements comprise at least one of the following:
a GPS receiver;
a barometer;
a thermometer; and
at least one pulse coil configured to measure heart rate; and the receiving device comprising a receiver configured to receive a transmission from the measurement device during the sports activity via a short-range wireless radio communication link, wherein the transmission includes sports activity information measured with the measurement device, a second memory configured to store at least one definition based on which a predefined set of pieces of sports activity information is selected from the received sports activity information, and a second processor configured to select the predefined set of pieces of sports activity information from the received sports activity information based on the at least one definition, which is defined based on the sport in question, stored on the second memory; and at least one feedback device, connected through a standard communication interface connection, configured to provide the at least one individual with feedback on a user interface display based on the selected sports activity information, wherein, in the case of at least one activity, the user interface display comprises activity-specific information comprising geophysical data selected from at least one of a group consisting of longitude and latitude, air pressure, heading, speed, temperature and graphical information, whereby the standard communication interface provides a capability to provide said display size, durability and usability according to the characteristic of said one activity.

23. The system according to claim 22, wherein the first processor is configured to calculate at least one additional piece of sports activity information based on the measured sports activity information; and the transmitter is configured to transmit the calculated sports activity information via a communication link to the receiving device.

24. The system according to claim 22, wherein the receiving device further comprises an output to which at least one feedback device can be connected.

25. The system according to claim 22, wherein the at least one feedback device is configured to provide at least one individual with at least one sports activity indicator based on the selected sports activity information.

26. The system according to claim 22, wherein the second processor is configured to calculate at least one additional piece of sports activity information based on the at least one selected sports activity information, and the at least one feedback device is configured to provide the at least one individual with the calculated at least one sports activity indicator.

27. The system according to claim 22, wherein the at least one feedback device is configured to present the at least one sports activity indicator to the at least one individual as at least one of a graphical form and voice signals.

28. The system according to claim 22, wherein the at least one feedback device comprises at least one of a display, a speaker and an earpiece.

29. Apparatus for providing at least one individual with feedback based on the measured sports activity information, the apparatus comprising:

means for measuring sports activity information with a measurement device comprising a plurality of measuring elements connected to a processing unit, the plurality of measuring elements comprising at least one of the following:
a GPS receiver;
a barometer;
a thermometer; and
at least one pulse coil configured to measure heart rate;

means, comprising a short-range radio communication link, for transmitting the measured sports activity information to a receiving device according to the use or purpose of the information for the sports activity, by transmitting the measured sports activity via the short-range wireless radio communication link during the activity;

means for selecting, based on the sport in question, from the received sports activity information a predefined set of pieces of sports activity information with the receiving device; and means, comprising a standard communication interface connection, for providing, with the receiving device on a user interface display, the at least one individual with feedback based on the selected sports activity information, wherein, in the case of at least one activity, the user interface display comprises activity-specific information comprising geophysical data selected from at least one of a group consisting of longitude and latitude, air pressure, heading, speed, temperature and graphical information, whereby the standard communication interface provides a capability to provide said display size, durability and usability according to the characteristic of said one activity.

* * * * *